United States Patent
Lewis et al.

(10) Patent No.: US 9,540,664 B2
(45) Date of Patent: Jan. 10, 2017

(54) SYSTEMS AND METHODS FOR IMPROVING ETHANOL YIELD

(75) Inventors: Stephen M. Lewis, Sioux Falls, SD (US); Neelakantam V. Narendranath, Sioux Falls, SD (US)

(73) Assignee: POET Research, Inc, Sioux Falls, SD (US)

( * ) Notice: Subject to any disclaimer, the term of this patent is extended or adjusted under 35 U.S.C. 154(b) by 35 days.

(21) Appl. No.: 14/004,897

(22) PCT Filed: Mar. 14, 2012

(86) PCT No.: PCT/US2012/029093
§ 371 (c)(1),
(2), (4) Date: Sep. 12, 2013

(87) PCT Pub. No.: WO2012/125739
PCT Pub. Date: Sep. 20, 2012

(65) Prior Publication Data
US 2013/0344557 A1     Dec. 26, 2013

Related U.S. Application Data

(60) Provisional application No. 61/452,407, filed on Mar. 14, 2011.

(51) Int. Cl.
*C12P 7/08* (2006.01)
*C12P 7/06* (2006.01)

(52) U.S. Cl.
CPC .. *C12P 7/08* (2013.01); *C12P 7/06* (2013.01); *Y02E 50/17* (2013.01)

(58) Field of Classification Search
None
See application file for complete search history.

(56) References Cited

U.S. PATENT DOCUMENTS 8,883,470 B2 † 11/2014 Pimentel
2009/0117634 A1* 5/2009 Bradley et al. ............... 435/165

OTHER PUBLICATIONS

International Search Report and Written Opinion mailed Aug. 20, 2012 for PCT Application Serial No. PCT/US2012/029093, 13 pages.
Graves, et al. "Effect of pH and lactic or acetic acid on ethanol productivity by *Saccharomyces cerevisiae* in corn mash" Journal of Industrial Microbiology & Biotechnology; Official Journal of the Society for Industrial Microbiology, 2006, Springer, Berlin, DE—ISSN 1476-5535 vol. 33, Nr:6, pp. 469-474.
Zhao, et al. "Application of acetate buffer in pH adjustment of sorghum mash and its influence on fuel ethanol fermentation" Journal of Industrial Microbiology & Biotechnology ; Official Journal of the Society for Industrial Microbiology, 2009, Springer, Berlin, DE—ISSN 1476-5535 vol. 36, Nr:1, pp. 75-85.
Casey, et al. "Effect of acetic acid and pH on the cofermentation of glucose and xylose to ethanol by a genetically engineered strain of *Saccharomyces cerevisiae*" FEMS Yeast Research, 2010, Wiley-Blackwell Publishing Ltd, GB, NL—ISSN 1567-1356 vol. 10, Nr:4, pp. 385-393.
European Office Action for European Patent Application No. 12 710 632.6-1501 Dated Jul. 8, 2014, 5 pages.

\* cited by examiner
† cited by third party

*Primary Examiner* — Karen Cochrane Carlson
*Assistant Examiner* — Jennifer M. H. Tichy
(74) *Attorney, Agent, or Firm* — Amin, Turocy & Watson, LLP

(57) ABSTRACT

Systems and methods for improving ethanol yield are provided. A feedstock is ground suitably fine for use in fermentation. The feedstock may include corn or any other suitable material. In some cases, the feedstock undergoes a fractionation prior to grinding. The ground feedstock may be slurried with water and enzymes to facilitate conversion of the starch in the feedstock to sugars. The slurry may be about 35% solids. After being slurried, an ethanologen may be added. Additionally, the pH of the slurry may be adjusted to between 4.2 and 5.2 to facilitate the priming A primer is added to the slurry. The primer may include any weak acid, and in some embodiments includes acetic acid. Acetic acid, when used as a primer, may be added at a concentration of between 1200 and 3600 parts per million. The slurry is fermented to produce improved yields of ethanol.

24 Claims, 12 Drawing Sheets

SYSTEMS AND METHODS FOR IMPROVING ETHANOL YIELD

CROSS-REFERENCE TO RELATED APPLICATIONS

This application is a U.S. national stage filing of Patent Cooperation Treaty (PCT) application serial number PCT/US2012/029093 entitled "SYSTEMS AND METHODS FOR IMPROVING ETHANOL YIELD" filed on Mar. 14, 2012, which claims the benefit of U.S. Provisional Application Ser. No. 61/452,407, filed Mar. 14, 2011, and entitled "SYSTEMS AND METHODS FOR IMPROVING ETHANOL YIELD", the entirety of which is expressly incorporated herein by reference.

FIELD

The subject disclosure relates to systems and methods for improving ethanol yield in an ethanol production facility.

BACKGROUND

Ethanol traditionally has been produced from grain-based feedstocks (e.g., corn, sorghum/milo, barley, wheat, soybeans, etc.), or from sugar (e.g., sugar cane, sugar beets, etc.).

In a conventional ethanol plant, corn, sugar cane, other grain, beets, or other plants are used as feedstocks and ethanol is produced from sugar (in the case of sugarcane or beets) or starch contained within the corn, or other plant feedstock. In a corn ethanol facility, corn kernels are cleaned and milled to prepare starch-containing material for processing. Corn kernels can also be fractionated to separate the starch-containing material (e.g., endosperm) from other matter (such as fiber and germ). Initial treatment of the feedstock varies by feedstock type. Generally, however, the starch and sugar contained in the plant material is extracted using a combination of mechanical and chemical means.

The starch-containing material is slurried with water and liquefied to facilitate saccharification, where the starch is converted into sugar (e.g., glucose), and fermentation, where the sugar is converted by an ethanologen (e.g., yeast) into ethanol. The fermentation product is beer, which comprises a liquid component, including ethanol, water, and soluble components, and a solids component, including unfermented particulate matter (among other things). The fermentation product is sent to a distillation system where the fermentation product is distilled and dehydrated into ethanol. The residual matter (e.g., whole stillage) comprises water, soluble components, oil, and unfermented solids (e.g., the solids component of the beer with substantially all ethanol removed, which can be dried into dried distillers grains (DDG) and sold, for example, as an animal feed product). Other co-products (e.g., syrup and oil contained in the syrup), can also be recovered from the whole stillage.

In a typical ethanol plant, a number of factors may impact the yield of ethanol produced during fermentation. These factors include the efficiency of the ethanologen, the amount of starch that is converted into sugar, pH and temperature effects, and the presence of inhibitors, to name a few. Ethanol production facilities are continually striving to increase ethanol yields in order to drive overall profitability. Particularly when the cost of the feedstock is high, increasing yields may have a substantial impact upon total plant profitability.

One method of increasing ethanol yield includes optimizing operational conditions to minimize the residual starch in the beer post fermentation. The rationale behind such a strategy is that any starch that is still present after fermentation could have been converted into sugar and subsequently converted into ethanol. These operational conditions include loading varying levels of solids, adjusting fermentation pH, temperature regimes, fermentation length, enzyme additions, ethanologen inoculation amount, etc. Another strategy for increasing the ethanol yield is the removal of compounds that inhibit the production of ethanol. Such inhibitors are traditionally identified as acetic acid, glycerol, and furfural, among many others.

What is not typically recognized, however, is that the energy utilization by the ethanologen also has a significant impact upon ethanol yield. Reducing residual starches and removing inhibitors may result in ethanol yield improvements, but these methods of yield improvement do not address the energy utilization issues of the ethanologen. For example, the ethanologen may utilize sugar generated from starch to generate Adenosine-5'-triphosphate (ATP) through glycolysis, thereby generating ethanol. The ATP generated is then utilized by the ethanologen for metabolic activities. However, it is also possible for the ethanologen to utilize sugar (e.g., glucose) for cell growth, or the generation of alternate organic byproducts. In these cases, the sugar is still consumed but is consumed without the generation of ethanol. This may also result in a reduction of residual starch, but may stifle ethanol yield.

SUMMARY

The disclosed aspects relate to systems and methods for improving the yield of ethanol produced at an ethanol production facility. Such systems and methods can provide enhanced ethanol titers thereby enabling an ethanol producer to obtain equal yields without adding as much feedstock, or enabling ultra high ethanol yields. The systems and methods can enable ethanol producers to achieve lower waste through reduced cell mass growth, thereby reducing glycerol production as well. Lower glycerol production may also improve flow-ability and reduce caking properties of co-products such as dried distiller's gains with solubles (DDGS).

In some embodiments, a feedstock is ground suitably fine for use in fermentation. The feedstock may include corn, or may include any other suitable material. In some cases, the feedstock may also undergo a fractionation prior to grinding. Grinding may be performed such that greater than 90% of the material is fines.

The ground feedstock (or fraction of the feedstock) can then be slurried with water and enzymes to facilitate the conversion of the starch in the feedstock to sugars. In addition, the slurry can include a backset such as thin stillage, clarified thin stillage or other reclaimed water source. The slurry can be about 35% solids, in some embodiments.

After being slurried, an ethanologen, such as *Saccharomyces cerevisiae*, can be added. Additionally the pH of the slurry can be adjusted to between 4.2 and 5.2 in order to facilitate the priming. A primer is then added to the slurry. The primer can include any weak acid, and in some embodiments includes acetic acid. Acetic acid, when used as a primer, can be added at a concentration of between 1200 and 2400 parts per million. The slurry is then fermented to produce ethanol.

In some alternate embodiments, after the grind is slurried with water and enzymes, some portion of the slurry is segregated. The ethanologen is added to the portion of the slurry, and the primer is also added to the portion. As the portion is smaller in volume than the entire slurry mixture, less primer is used to achieve a desirable concentration. After holding the concentration of the primer in a desirable range for a critical period of time, the remainder of the slurry may be added back to the portion. The entire slurry volume may then be fermented.

Note that the various features of the disclosed aspects described herein may be practiced alone or in combination. These and other features of the disclosed aspects will be described in more detail below in the detailed description and in conjunction with the following figures.

DESCRIPTION OF THE DRAWINGS

In order that the various aspects may be more clearly ascertained, some embodiments will now be described, by way of example, with reference to the accompanying drawings, in which.

DETAILED DESCRIPTION

Figure 1:
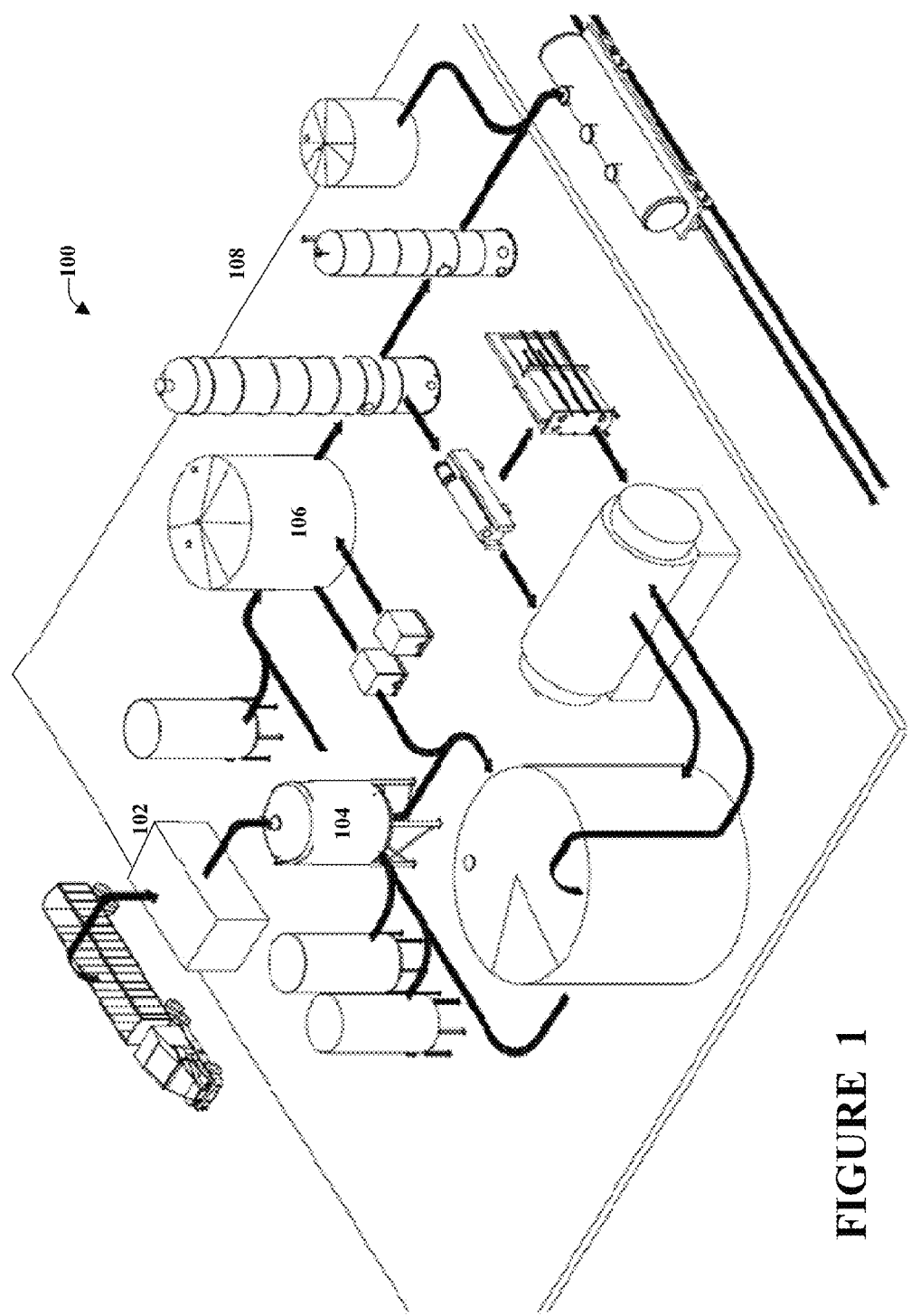
FIG. 1 is a perspective view of a biorefinery comprising an ethanol production facility, in accordance with some embodiments.

The various aspects will now be described with reference to several embodiments thereof as illustrated in the accompanying drawings. In the following description, numerous specific details are set forth in order to provide a thorough understanding of embodiments of the various aspects. It will be apparent, however, to one skilled in the art, that embodiments may be practiced without some or all of these specific details. In other instances, well known process steps and/or structures have not been described in detail in order to not unnecessarily obscure the disclosed aspects. The features and advantages of embodiments may be better understood with reference to the drawings and discussions that follow.

The disclosed aspects relate to systems and methods for improving ethanol yield using traditional grain feedstocks at an ethanol production plant. In a typical ethanol plant, a number of factors may impact the yield of ethanol produced during fermentation. These factors include the efficiency of the ethanologen, the amount of starch that is converted into sugar, pH and temperature effects, and the presence of inhibitors, to name a few. Ethanol production facilities are continually striving to increase ethanol yields in order to drive overall profitability. Particularly when the cost of the feedstock is high, increasing yields may have a substantial impact upon total plant profitability.

In some embodiments, an ethanol plant may "prime" the ethanologen in order to shift the energy utilization of the ethanologen away from cell mass production to the production of greater amounts of Adenosine-5'-triphosphate (ATP) for cellular activity. In typical fermentation conditions, ATP is produced through the anaerobic glycolysis of sugars. Ethanol is produced as a waste product of this metabolic activity. By placing a demand upon the ethanologen for ATP, the organism may be forced to produce greater amounts of ethanol. In addition to the greater levels of ethanol being produced, priming also reduces the generation of glycerol by the ethanologen (glycerol production corresponds to cell growth). The reduction of glycerol may impact downstream co-products, such as dried distiller's grains with solubles (DDGS) by increasing flow-ability and reducing caking. Specifics of driving the ethanologen to produce more ethanol, through priming, are provided in more detail below.

As discussed above, in an ethanol production facility, the ethanologen can be induced to generate greater quantities of ATP, and therefore ethanol, while reducing the production of cell mass or other organic byproducts. In addition to the increase in possible ethanol produced, by reducing the amount of cell growth by the ethanologen, a corresponding reduction in glycerol production is achievable. Reduced glycerol may have a positive impact on drying of dried distillers grains (DDG), and may also improve DDG flowability and susceptibility to caking.

Given the competitive market for ethanol production facilities, the disclosed aspects provide for systems and methods that improve ethanol yield through ethanologen activity coercion. Such systems and methods can provide substantial increase in ethanol yield in a cost efficient manner without requiring additional feedstock inputs, and without reduce glycerol production.

Referring to FIG. 1, an example biorefinery 100 comprising an ethanol production facility configured to produce ethanol from corn is shown. The example biorefinery 100 comprises an area 102 where corn (or other suitable material including, but not limited to, biomass, sugars, and other starch products) is delivered and prepared to be supplied to the ethanol production facility. The ethanol production facility comprises apparatus 104 for preparation and treatment (e.g., milling) of the corn into corn flour suitable for fermentation into fermentation product in a fermentation system 106. The ethanol production facility comprises a distillation system 108 in which the fermentation product is distilled and dehydrated into ethanol. The biorefinery may also comprise, in some embodiments, a by-product treatment system (shown as comprising a centrifuge, a dryer, and an evaporator).

Figure 2:
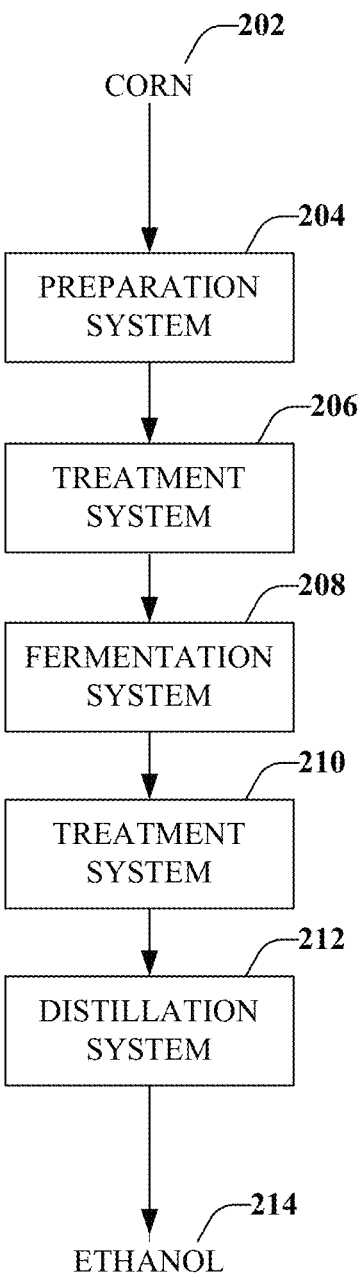
FIGS. 2 and 3 are process flow diagrams illustrating examples of ethanol production processes from corn to ethanol, in accordance with some embodiments.
Figure 3:
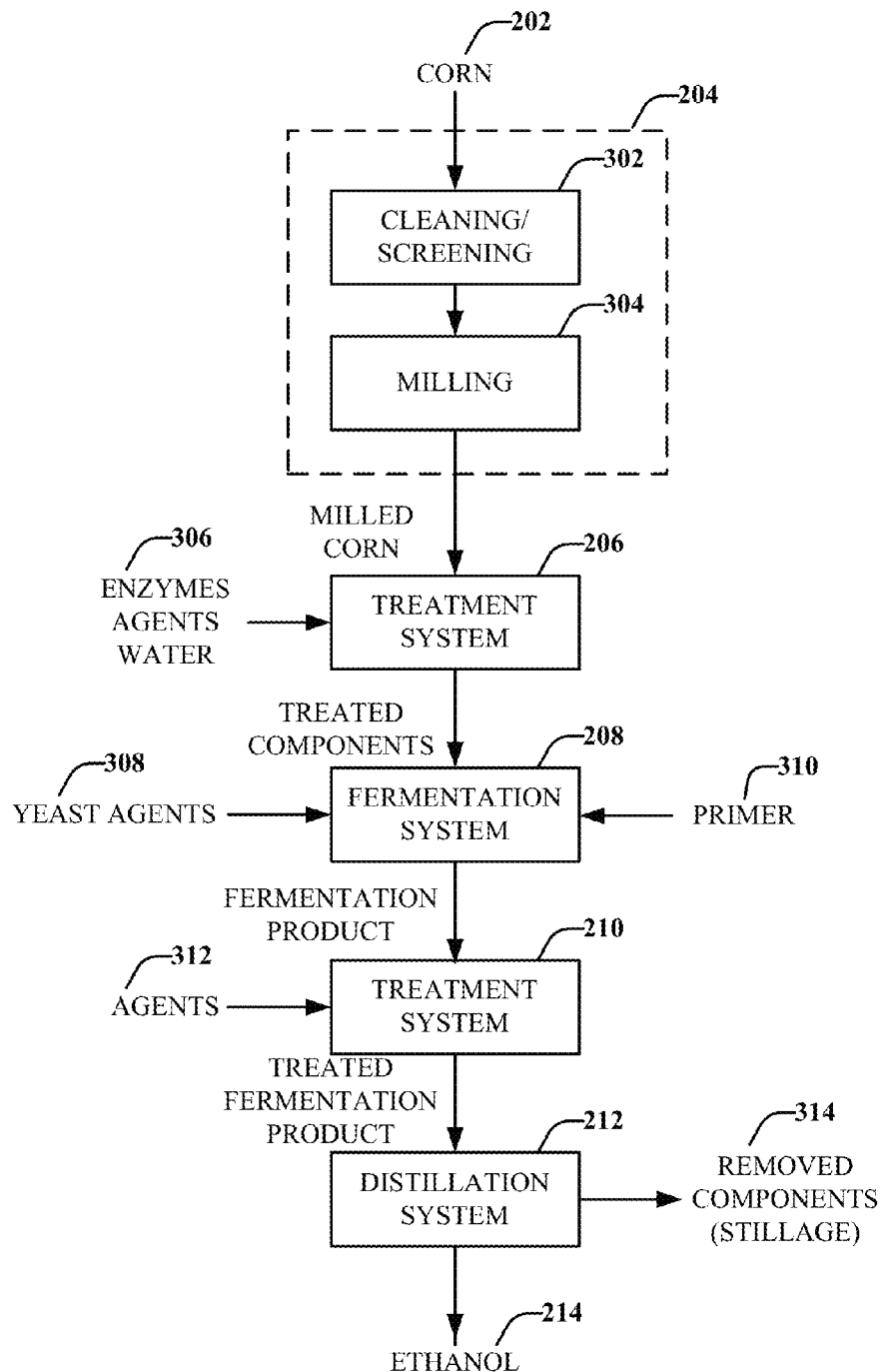

Referring to FIGS. 2 and 3, in an ethanol production process, corn 202 (or other suitable feed material) may be prepared for further treatment in a preparation system 204. As illustrated in FIG. 3, the preparation system 204 may comprise cleaning or screening 302 to remove foreign material, such as rocks, dirt, sand, pieces of corn cobs and stalk, and other unfermentable material (e.g., removed components). After cleaning or screening 302, the particle size of corn may be reduced by milling 304 to facilitate further processing. The corn kernels may also be fractionated into starch-containing endosperm, fiber, and germ, in accordance with some embodiments. The milled corn or endosperm is slurried with water, enzymes and agents 306 to facilitate the conversion of starch into sugar (e.g. glucose), such as in a first treatment system 206. The sugar (e.g., treated component) is converted into ethanol by an ethanologen (e.g. yeast or other agents 308) in a fermentation system 208.

The fermentation system 208 may likewise receive the "primer" 310 that drives the ethanologen to produce greater amounts of ATP during fermentation. In some embodiments, the primer may include a low dosage of acetic acid. In some alternate embodiments, the priming agent may include another weak acid. In yet other embodiments, the primer may include an aldehyde such as formaldehyde or acetaldehyde. In some embodiments where the primer is acetic acid, the acetic acid enters the ethanologen through passive diffusion. Once the acetic acid is in the ethanologen, the hydrogen ion may dissociate. This results in a buildup of hydrogen ions within the ethanologen (with an associated intracellular pH drop). The ethanologen may need an intracellular pH of near neutral to function properly, thus it expels the accumulated hydrogen ions via a proton pump (H+-ATPase). The proton pump may need expenditure of ATP, and thus drives the ethanologen to undergo glycolysis, in these embodiments. This causes an increase in ethanol produced during fermentation.

The product of fermentation (fermentation product) is beer, which comprises a liquid component, including the ethanol and water and soluble components, and a solids component, including unfermented particulate matter (among other things). The fermentation product may be treated with agents 312 in a second treatment system 210.

The treated fermentation product is sent to a distillation system 212. In the distillation system 212, the (treated) fermentation product is distilled and dehydrated into ethanol 214. In some embodiments, the removed components 314 (e.g., whole stillage), which comprise water, soluble components, oil and unfermented solids (e.g., the solids component of the beer with substantially all ethanol removed), may be dried into dried distillers grains (DDG) in a third treatment system (where the removed components may be treated with agents) and sold as an animal feed product. Other co-products, for example, syrup (and oil contained in the syrup), may also be recovered from the stillage. The thin stillage, that results when solids are removed from the whole stillage, can be used as a backset during the fermentation process and also can be used to increase the protein content of DDGS (Distillers Dried Grains with Solubles).

Figure 4:
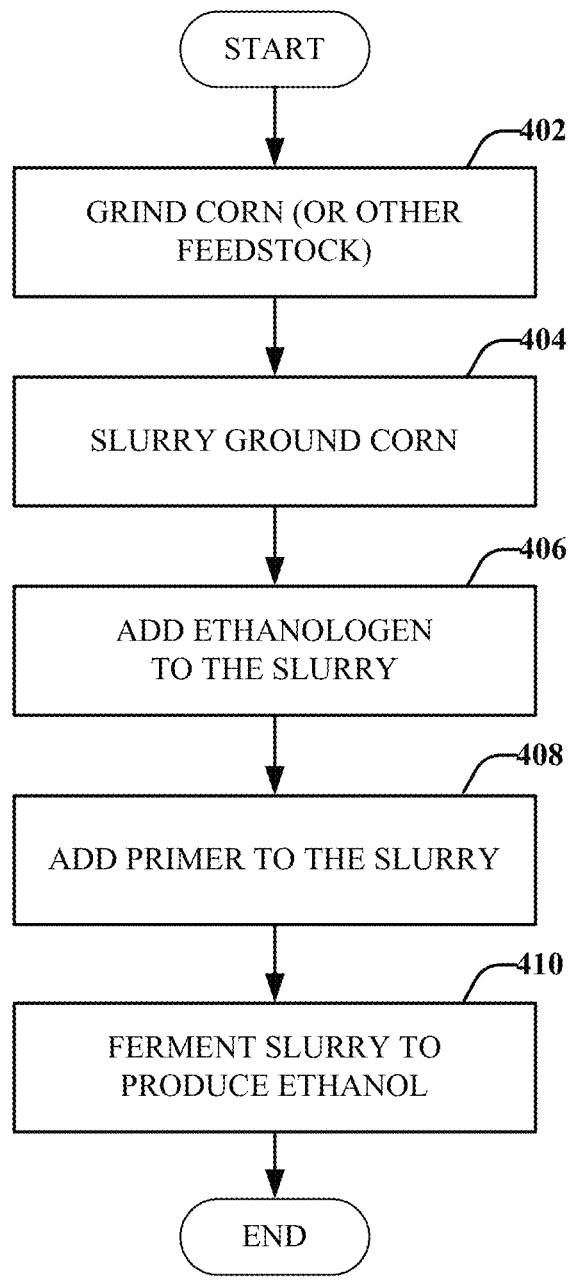
FIG. 4 is an example flowchart illustrating a first process for improving ethanol yields, in accordance with some embodiments.

Referring now to FIG. 4, which is an example flowchart illustrating a first process for improving ethanol yields, in accordance with some embodiments. In this example flowchart, the process begins with the grinding (at 402) of the corn, or other suitable feedstock. In some embodiments, the entire corn kernel is ground for fermentation. In some other embodiments, the corn kernel may be fractionated into its component parts, and only the starchy endosperm is ground for use in fermentation.

The ground corn, or other feedstock, may then be slurried (at 404) with water, enzymes, and other agents in order to facilitate the conversion of the starch into fermentable sugars. In some embodiments, the slurry is performed at low temperature in a "raw starch" hydrolysis. In some alternate embodiments, the slurry may be heated or otherwise cooked in order to facilitate the conversion of starch to sugars. In some embodiments, the slurry may be performed such that the final slurry material is around 35% solids, however any solids content is considered within the scope of some embodiments. Further, it is considered within the scope of some embodiments that any suitable feedstock, subjected to virtually any suitable pretreatment, may be primed in the manners disclosed in order to improve ethanol yields.

After the feedstock has been slurried, in this example process, the pH of the slurry mixture may be adjusted to optimize the priming efficiency. In some embodiments, the pH may be adjusted to anywhere between 4.2 and 5.4 for priming to have a positive effect. In some cases, the lower pH (e.g., 4.2-4.7) may benefit the priming by reducing the glycerol being produced. Ethanol increases become a more dominant benefit as the pH is raised (e.g., between 4.7 and 5.4). In some embodiments, a pH of between 4.8-5.2 may be particularly suited to optimize the benefits of priming on ethanol yields, and glycerol reduction.

The ethanologen may then be added (at 406) to the slurry. The ethanologen is often a yeast, such as *S. cerevisiae*. Additional components, such as nutrients, may also be added to the slurry. Then, the primer may be added (at 408) to the slurry. As previously noted, the primer may include a weak acid, such as acetic acid. The pH used to maximize priming efficiency may be dependent upon the weak acid being utilized. For example, when using acetic acid as the priming agent, a pH of about 4.7 to 5.2 may be employed to achieve the greatest ethanol yield increase. Other weak acids may perform better at differing pH values, dependent upon, to some degree, the $pK_a$ of each acid. Additionally, the dosage of the primer may be adjusted based upon its efficiency. Again, for example, when using acetic acid as the primer, it may be beneficial to prime at about 1600 to 2000 parts per million (ppm). Of course, the priming dosage may depend upon the primer used.

The slurry may be held at temperatures to facilitate the production of ethanol for a determined period of time during the fermentation (at 410). After fermentation, the beer may be subjected to further treatment and/or distillation to recover the ethanol generated.

Figure 5:
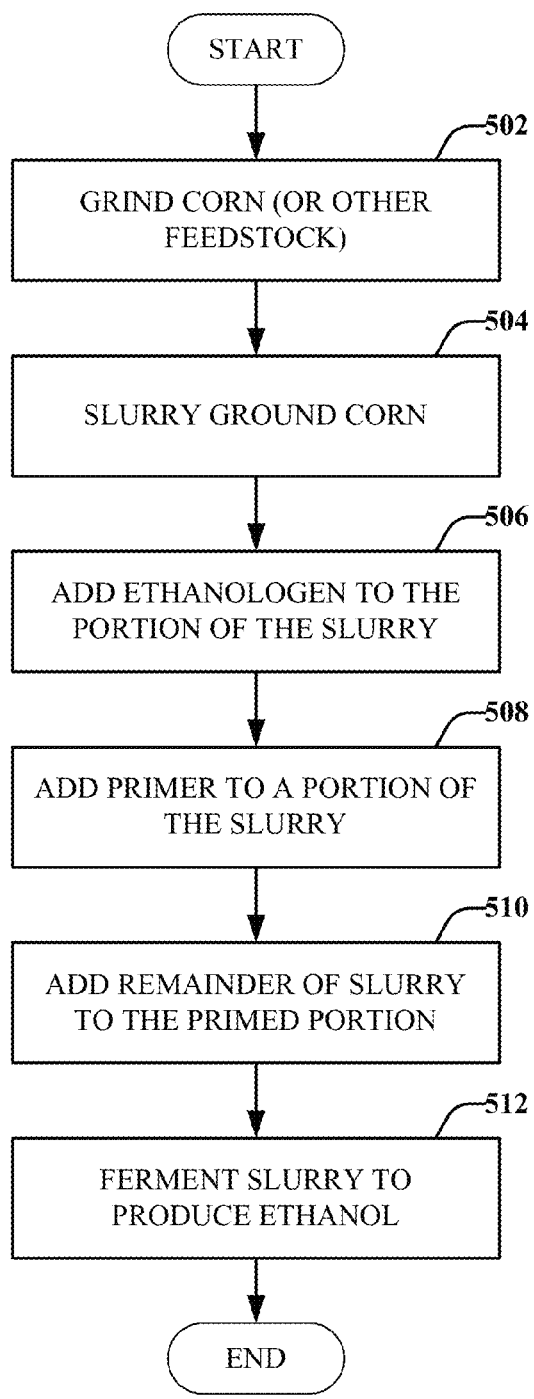
FIG. 5 is an example flowchart illustrating a second process for improving ethanol yields, in accordance with some embodiments.

Now referring to FIG. 5, which is an example flowchart illustrating a second process for improving ethanol yields, in accordance with some embodiments. The process described in relation to FIG. 5 differs from that of FIG. 4 in that the initial propagation of the ethanologen is primed for only a relatively short period of time. This process may be particularly useful when the fermentation is very large, and thus a much lower amount of primer is utilized to achieve a significant ethanol yield benefit.

In this alternate process, the corn (or other feedstock) is ground (at 502). This grinding may include whole grain grinding or may include a fractionation and grinding of the starch-containing portion of the grain. The ground corn may be slurried (at 504) with water (or other backset), agents and enzymes in order to convert the starch to sugar. The slurry may be made such that it is about 35% solids, but as previously noted, the percent solids may vary dependent upon feedstock used and other process considerations. The ethanologen may be added (at 506) to some portion of the slurry. In a typical ethanol production facility, the fermentation tank is filled with the slurry over a long period of time due to the large volume. Often the ethanologen propagation is added during the fermentor tank fill. By adding the ethanologen propagation mid-fill, the ethanologen can become well mixed with the slurry. Additionally, this provides the ethanologen a longer period of time with the slurry to ferment the sugars into ethanol. Lastly, by partially filling the fermentor first, the chance that the ethanologen is inhibited or damaged by tank residues can be dramatically reduced.

It has been found, in some embodiments, that there may be a critical period of time where priming should be performed in order to increase its efficiency. This critical time window enables an ethanol production facility to operate normally by filling the fermentor tank with slurry, adding the ethanologen propagation after a set period of time, and then adding the primer (at 508) soon thereafter, in order to achieve a substantial increase in ethanol yields. Since there is a critical window for priming, the portion of the slurry is all that needs to be primed to the desired concentration of primer. As the fill progresses this concentration is reduced. However, since the priming concentration was high enough during the critical window, most of the priming effect is realized even though the final concentration of the primer, once the fermentor is full, is much lower. This effect enables the ethanol producer to utilize a greatly reduced quantity of the primer, and still achieve almost all of the priming yield increase.

After priming, the remainder of the slurry may be added (at 510) to the primed portion (e.g., finishing fermentor fill). The fermentation is then performed (at 512) according to temperature and timing protocols. The product of the fermentation may be subjected to some further treatments, and distilled to recover the ethanol.

As disclosed herein, a method for improving ethanol yield is provided. The method comprises grinding a feedstock to generate a grind and combining the grind with water and enzymes to produce a slurry. The starch in the grind is converted to sugars in the slurry. The method also comprises adjusting the pH of the slurry to facilitate priming and adding an ethanologen to the slurry. Further, the method comprises priming the slurry by adding a priming agent and fermenting the slurry to produce ethanol.

Another aspect relates to a method for improving ethanol yield. The method comprises grinding a feedstock to generate a grind and combining the grind with water and enzymes to produce a slurry. Starch in the grind is converted to sugars in the slurry. The method also comprises removing a portion of the slurry, thereby leaving behind a remainder of the slurry and adjusting the pH of the portion of the slurry to facilitate priming An ethanologen is added to the portion of the slurry and the portion of the slurry is primed by adding a priming agent. Further, the method comprises combining the portion of the slurry with the remainder of the slurry and fermenting the slurry to produce ethanol.

A further aspect disclosed herein, relates to a method for improving ethanol yield in a commercial scale ethanol plant. The method comprises grinding a feedstock to generate a grind and combining the grind with water and enzymes to produce a slurry. Starch in the grind is converted to sugars in the slurry. The method also comprises to begin filling a fermentation tank with the slurry. The fermentation tank can be commercial scale between 200,000 and 750,000 gallons. The method also comprises adding an ethanologen to the fermentation tank and adding between about 100 to 350 pounds of acetic acid to the fermentation tank approximately 30 minutes to two hours after the adding of the ethanologen. The method also comprises to continue filling the fermentation tank with the slurry and fermenting the slurry to produce ethanol.

A series of limited examples were conducted according to an exemplary embodiment of the system (as shown in FIG. 3) in an effort to determine suitable apparatus and operating conditions for the priming of a fermentation to increase yields of ethanol produced. The following examples are intended to provide clarity to some embodiments of systems and means of operation; given the limited nature of these examples, they do not limit the scope of the invention.

Example 1

In this example a range of different dosages of acetic acid were added to a standard non-cooked (raw starch hydrolysis) fermentation and the effects were studied at three different initial pH levels. The acetic acid levels chosen were: 0, 0.05, 0.1, 0.2, and 0.3% w/v and the initial pH levels chosen were 4.2, 4.7, and 5.2. The entire experiment was conducted in duplicate.

In this experiment, corn that was ground using a hammer mill to >90% fines was obtained from a nearby biorefinery. A 36% dry solids slurry of ground corn and water was prepared. The slurry (~70 mL) was prepared by weighing out the appropriate amount of corn and water into each individual reactor. Lactoside247™ was added at 2.5 ppm to prevent any lactic acid bacterial contamination. Urea was added ~0.24 g/L (4 mM) for a nitrogen source. The different doses of acetic acid were added to the reactors and each set of the reactors were pH adjusted to 4.2, 4.7, and 5.2 using either 10% v/v sulfuric acid or 45% w/w potassium hydroxide.

A raw starch hydrolyzing enzyme blend was added at 0.2 g/L. Everything was added to the reactor in such a way that the final volume in the reactor was 70 mL. Then, the appropriate amounts of yeast was added to the reactors, mixed well, and the reactors were placed in a circulating water bath at 31.1° C. (88° F.). A typical temperature staging protocol was used throughout the 88 hr fermentation which ended at 27.8° C. (82° F.). Samples were withdrawn at 0, 24, 48, 72, and 88 hr of fermentation and analyzed for sugars, glycerol, organic acids and ethanol using HPLC.

About 4 mL of sample was withdrawn at each time point. These samples were centrifuged at 4500 rpm for 2 min. The supernatant was then filtered through a 0.2 µpore size filter into HPLC vials. The vials were loaded into an auto-sampler (Waters separations module 717 plus or 2695). An aliquot (5 µL) of the sample was injected by the auto-injector onto a reverse phase column (HPX-87H from BioRad Laboratories) maintained at 50° C. Aqueous sulfuric acid at 0.005M was used as the mobile phase (eluent). The HPLC system was fitted with a refractive index detector (Waters model 2410 or 2414). The components (sugars, organic acids, and ethanol) were identified and quantified using Waters Empower software.

Figure 6:
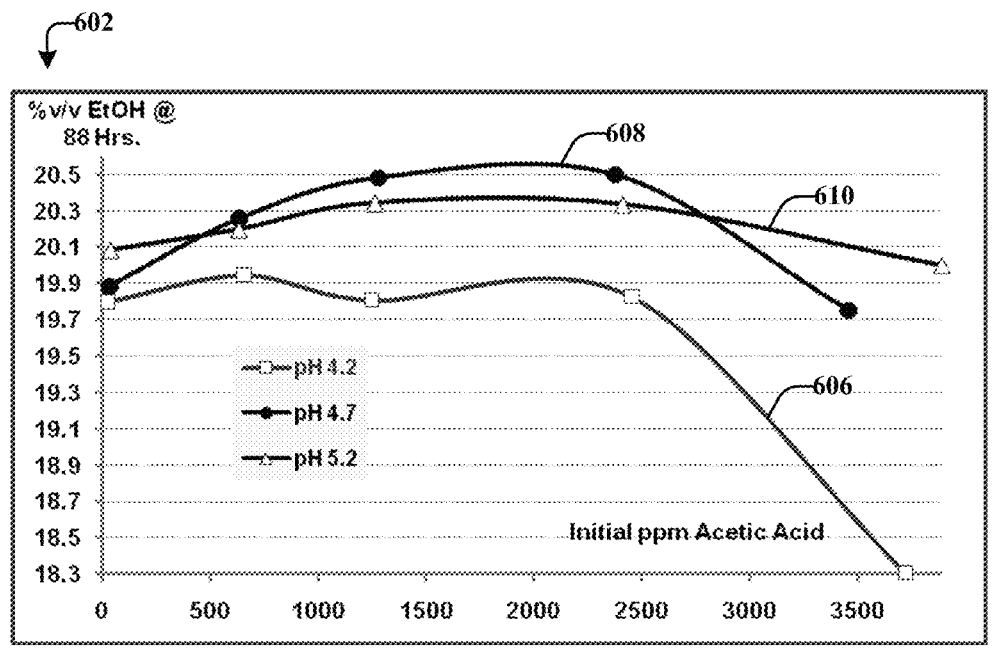
FIG. 6 is an example graph diagram illustrating the percentage of ethanol generation dependent upon primer dosage, in accordance with some embodiments.

Clear trends were observed with increasing acetic acid concentrations. The results of the experiment are illustrated with reference to FIG. 6 where an example graph is provided that details the results. In this example graph, the ethanol yields are on the vertical axis 602, and the concentration of acetic acid is provided on the horizontal axis 604. Lines for the experiments at pH 4.2, 4.7, and 5.2 are illustrated at 606, 608, and 610 respectively.

There was a definite interaction observed between pH and acetic acid concentration. In this example experiment, at the pH levels tested, pH of 4.7 appeared to be better for obtaining a maximum benefit in ethanol production. A concentration of 0.12% to 0.24% (1200-2400 ppm) acetic acid provided increased ethanol titers when the initial pH was 4.7 or 5.2. No major benefits were observed when the initial pH was 4.2. At the highest concentration of acetic acid tested (0.37% w/v), an inhibitory effect was observed especially in the reactors set at pH 4.2.(The actual acetic acid concentrations were 0, 0.6, 0.12, 0.24, 0.37% w/v). In the same study, significant reduction in glycerol production was also observed. Maximum reduction in glycerol of over 50% was observed in fermentations set at pH 4.7 when the initial acetic acid concentration was 0.24% w/v. These were the conditions that had the highest ethanol titer of 20.5% v/v.

Figure 8:
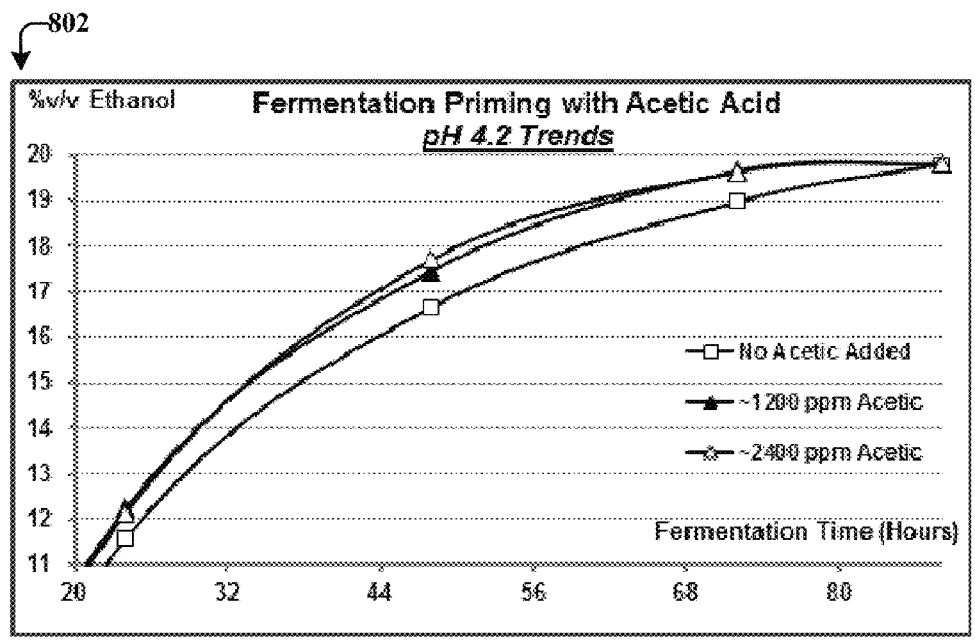
FIG. 8 is an example graph diagram illustrating the percentage of ethanol generation dependent upon fermentation length for various doses of primer at a low pH, in accordance with some embodiments.

FIG. 8 provides an example graph for the percent ethanol on the vertical axis 802 compared by length of fermentation on the horizontal axis 804 for fermentations performed at an initial pH of 4.2. Curves are provided for representative priming concentrations tested. As illustrated in the graph, a primer dosage between 1200 and 2400 ppm acetic acid provides a fermentation benefit early on, with the lower primer dosages catching up after 70 hours of fermentation.

Figure 9:
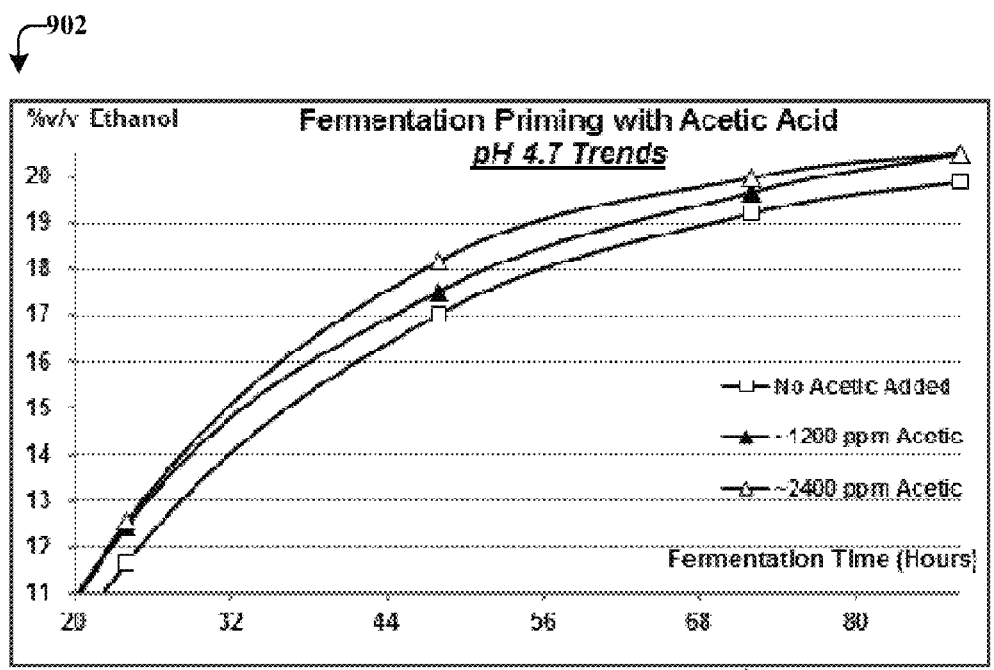
FIG. 9 is an example graph diagram illustrating the percentage of ethanol generation dependent upon fermentation length for various doses of primer at a mid level pH, in accordance with some embodiments.

FIG. 9 provides an example graph for the percent ethanol on the vertical axis 902 compared by length of fermentation on the horizontal axis 904 for fermentations performed at an initial pH of 4.7. Curves are provided for representative priming concentrations tested. As illustrated, a primer dosage between 1200 and 2400 ppm acetic acid provides a fermentation benefit throughout fermentation.

Figure 10:
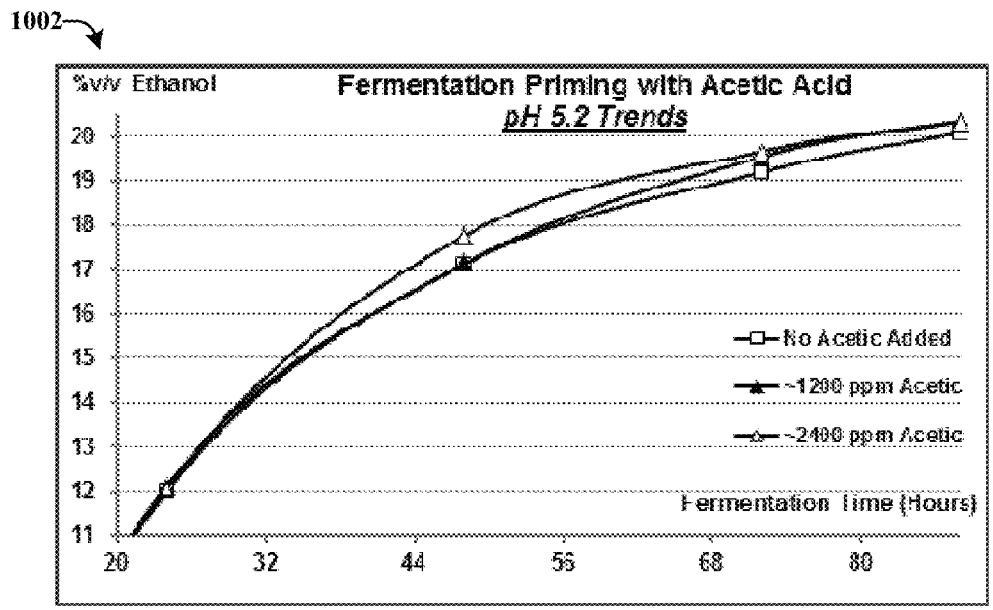
FIG. 10 is an example graph diagram illustrating the percentage of ethanol generation dependent upon fermentation length for various doses of primer at a higher pH, in accordance with some embodiments.

FIG. 10 provides an example graph for the percent ethanol on the vertical axis 1002 compared by length of fermentation on the horizontal axis 1004 for fermentations performed at an initial pH of 5.2. Curves are provided for priming concentrations tested. As illustrated, a primer dosage between 1200 and 2400 ppm acetic acid provides a slight fermentation benefit throughout fermentation.

In addition to effects on ethanol production yields, priming with acetic acid also had an effect upon glycerol production. The main reason for glycerol production in S. cerevisiae (when grown on glucose) is due to the need to reoxidize NADH. This occurs when pyruvate from the glycolytic pathway is channeled to biosynthetic reactions (cell mass production). In the presence of acetic acid, (under fermentation conditions), the cell mass yield from ATP is reduced as most of the ATP (generated via glycolysis) is used up by the plasma membrane ATPase to pump out the excess protons (caused by dissociation of acetic acid in the cell).

Figure 7:
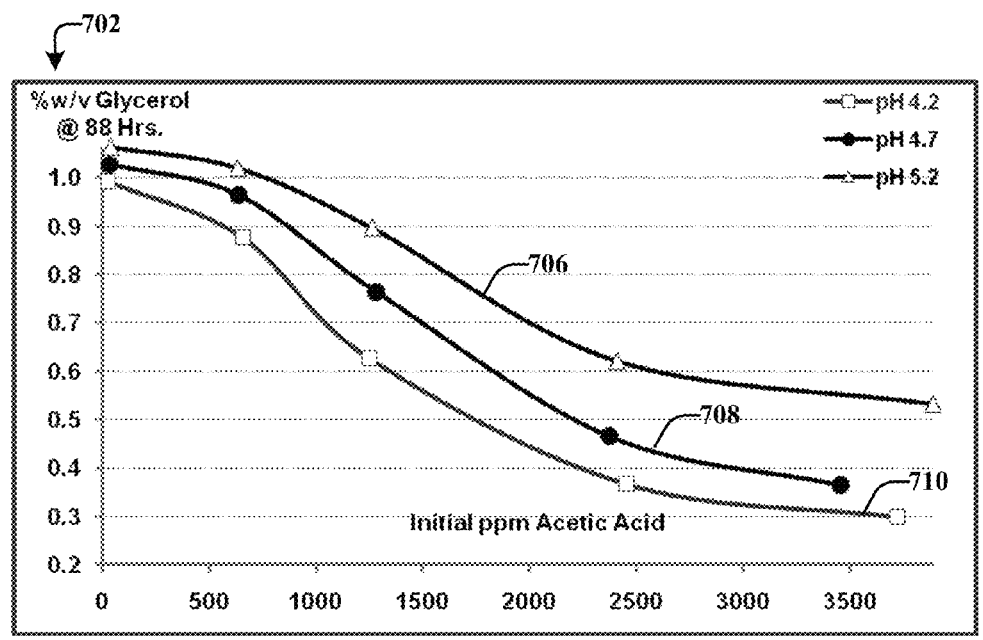
FIG. 7 is an example graph diagram illustrating the percentage of glycerol generated dependent upon primer dosage, in accordance with some embodiments.

FIG. 7 provides example results of the effect of priming on glycerol production. In this example graph, glycerol concentration is labeled on the vertical axis 702, while the horizontal axis 704 reflects the acetic acid concentration. Lines for pH concentration of 5.2, 4.7, and 4.2 are also provided, at 706, 708, and 710 respectively.

In this example experiment, it was observed that there was substantial reduction in yeast biomass in primed samples. All samples had an initial inoculation of approximately $1 \times 10^7$ cells/mL mash. After 24 hours at 88° F. (31.1° C.), samples were withdrawn to analyze for yeast cell counts. The samples were serially diluted and appropriate dilutions were plated on to Yeast extract-Malt extract (YM) agar plates. The plates were incubated at 30° C. and the colonies formed were counted after 48 h. The results were expressed as colony forming units (CFU) per mL.

Figure 12:
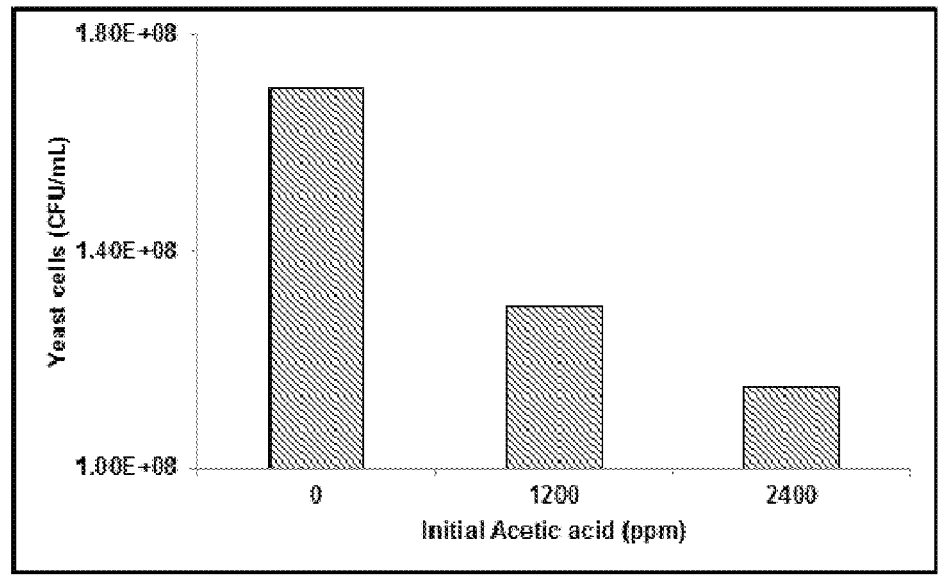
FIG. 12 is an example graph diagram illustrating cell growth dependent upon acid priming dosage, in accordance with some embodiments.

FIG. 12 is an example graph diagram illustrating cell growth dependent upon acid priming dosage, in accordance with some embodiments. Yeast cell count is indicated on the vertical axis 1202, and histogram bars are provided for each sample on the horizontal axis 1204. Samples tested include a control with no acetic acid addition, and samples treated at 1200 ppm and 2400 ppm respectively.

The results showed that there was a significant reduction is yeast cell counts in the presence of acetic acid. About 24% and 32% reduction in cell counts were observed when the initial acetic acid levels in the mash were 1200 and 2400 ppm acetic acid, respectively.

In some embodiments, due to this decreased cell mass yield, a decreased glycerol yield is also observed. As more of the pyruvic acid is not used for biosynthetic reactions, the pyruvateremains available for ethanol production during which the NADH can be reoxidized, thereby eliminating the need for glycerol production.

Figure 11:
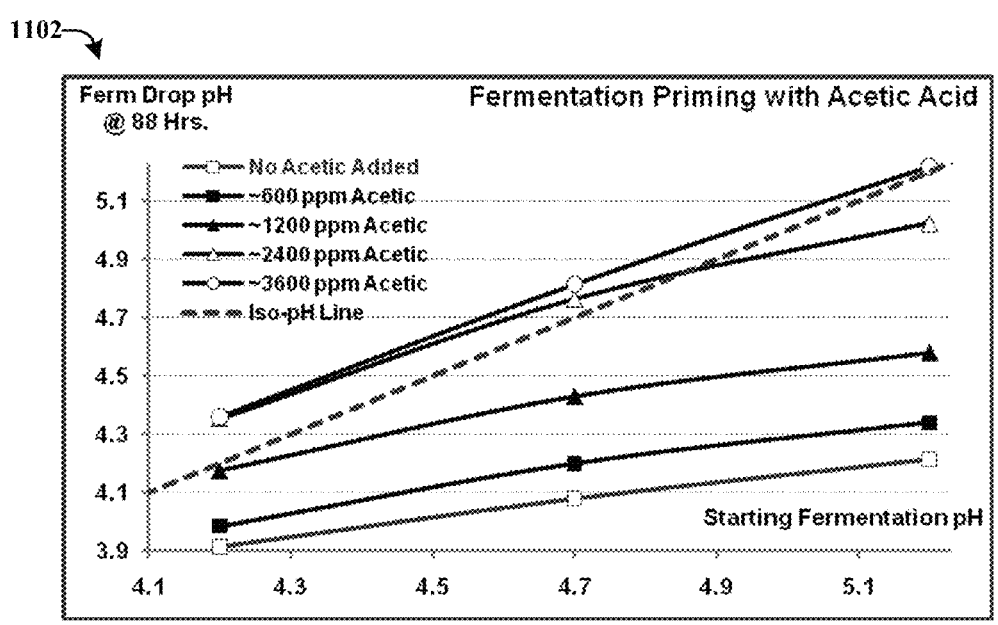
FIG. 11 is an example graph diagram illustrating the pH of the fermentation broth after fermentation as compared to pre-fermentation pH for various doses of primer, in accordance with some embodiments.

Lastly, the pH of each sample was measured after the fermentation. Results of this pH measurement are provided in the example graph illustrated in FIG. 11. In this example graph, the pH of the sample after fermentation is provided on the vertical axis 1102, and the initial pH is provided on the horizontal axis 1104. A dotted line indicating no change in pH is also illustrated. Curves are plotted relating to the dosage of acetic acid added.

In this example experiment, there was not a major shift in the final pH at the end of fermentation in reactors set at pH 4.7 that had an initial acetic acid concentration of 0.24% w/v (2400 ppm). This is likely due to the $pK_a$ of acetic acid (4.74) which makes the added acetic acid behave as a buffer in the fermentation system.

These results suggest that acetic acid can be used at low concentrations of 0.12-0.24% w/v (1200-2400 ppm) at pH 4.7 at the beginning of fermentation in a raw starch hydrolysis process. At these concentrations, the acetic acid improves the rate of fermentation, increases the final ethanol titers and yield, and significantly reduces glycerol production by the yeast. This reduction in glycerol can have a substantial impact on the flowability of DDGS by reducing caking.

Example 2

In this second example, an attempt is made to evaluate the stimulatory effects of acetic acid in sugarcane or molasses fermentations where sucrose is the main carbon source for the yeast. For this example, a laboratory media with sucrose was used. The media used was Yeast extract-Peptone (YP) broth supplemented with 20% w/v (200 g/L) sucrose. An acetic acid dose response (at 500, 1000, 1500, 2000, 2500, and 3000 ppm) was conducted. Control with no added acetic acid was also included. The fermenters were pH adjusted to 4.5 and after yeast inoculation the fermentations were carried out for 30 hours at 32° C. After 30 h, samples were withdrawn and analyzed for sugars, organic acids, and ethanol. Samples were also withdrawn at 24 h and yeast growth was monitored by optical density measurement at 600 nm.

Figure 13:
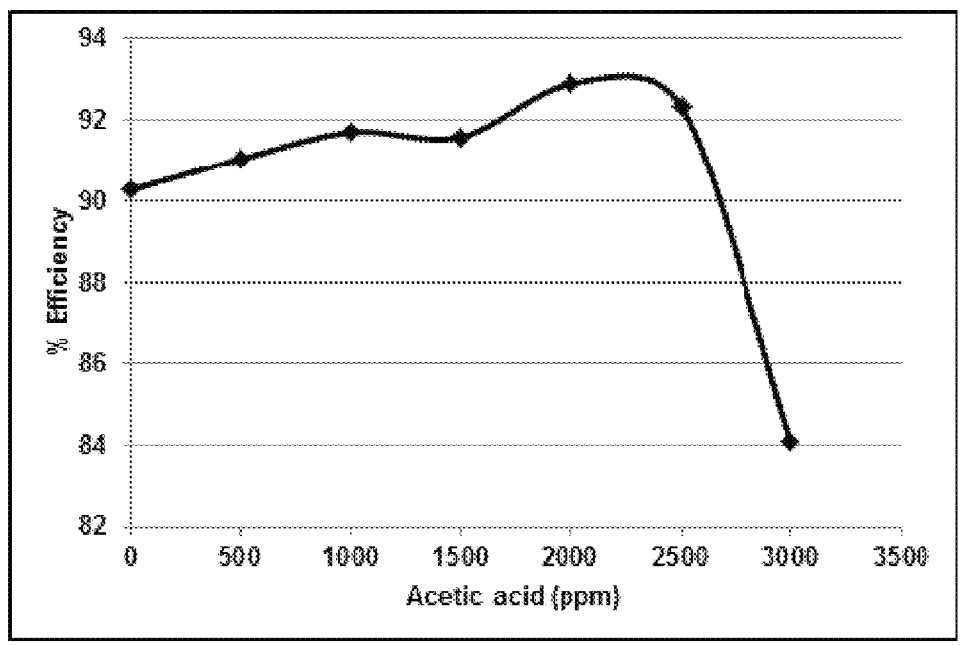
FIG. 13 is an example graph diagram illustrating fermentation efficiency of sucrose dependent upon acid priming dosage, in accordance with some embodiments.

The results obtained suggest that a stimulatory effect is observed when the initial acetic acid concentration in the medium is between 2000 and 2500 ppm (2-2.5 g/L) as illustrated FIG. 13. Percent ethanol conversion efficiency is illustrated on the vertical axis 1302, and acetic acid levels are illustrated on the horizontal axis 1304. Increased acetic acid concentrations up to 2500 ppm appear to have a similarly stimulatory effect on ethanol production when a sucrose sugar source is utilized. Notably, above 2500 ppm concentrations the acetic acid becomes inhibitory to fermentation, and efficiency drops off rapidly at these higher concentrations.

Figure 14:
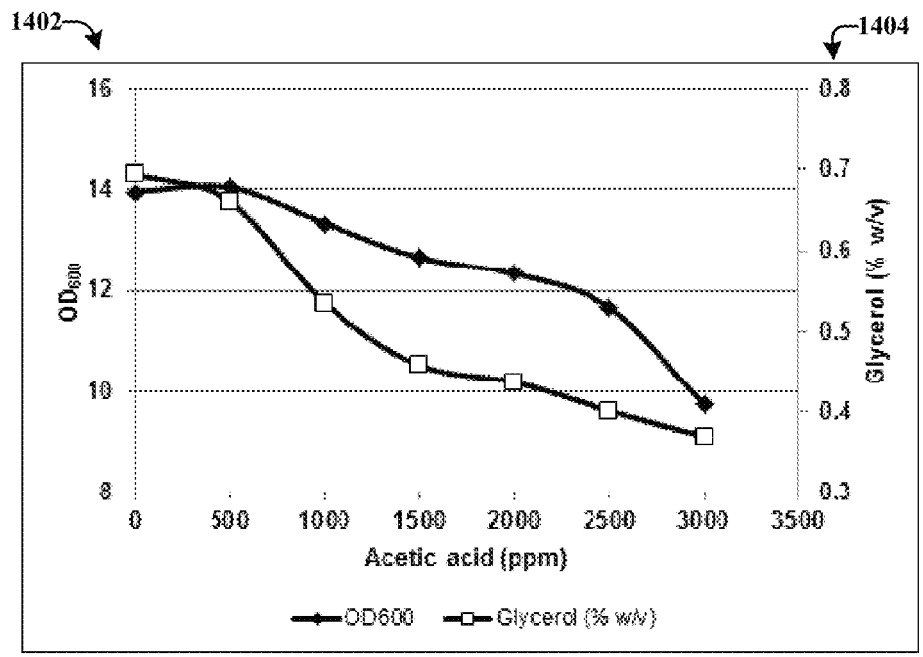
FIG. 14 is an example graph diagram illustrating yeast cell mass and glycerol levels dependent upon acid priming dosage after fermentation, in accordance with some embodiments.

FIG. 14 illustrates the yeast cell mass as measured by optical density (OD) at 600 nm after 24 hours of fermentation and final glycerol concentration in YP sucrose media supplemented with acetic acid at various levels. One vertical axis 1402 indicates optical density which is linearly related to yeast cell mass. The second vertical axis 1404 indicates glycerol levels after the fermentation. The horizontal axis 1406 indicates acetic acid concentration.

As shown, when acetic acid is used at such low levels under fermentation conditions, an increase in the fermentation rate is observed. The reason for which is the need for ATP generation to pump the excess protons (caused by dissociation of acetic acid within the yeast cell) out of the cell. Since most of the ATP is used by the ATPase to pump out the excess protons, lesser cell mass is produced for similar levels of end product (ethanol) made by the yeast. This lesser cell mass in the presence of acetic acid results in lower glycerol production by the yeast.

Example 3

In this third example, the stimulatory effects of formaldehyde are confirmed. Standard laboratory cold cook fermentations were set up. As in earlier examples, corn flour was slurried in water to make up a mash of 34% dry solids. The pH of the mash was adjusted to 4.5.

Various levels of formaldehyde were added to the fermenters. Yeast was inoculated after adding the raw starch enzymes and fermentations were carried out for 88 hours following a standardized temperature staging protocol.

Figure 15:
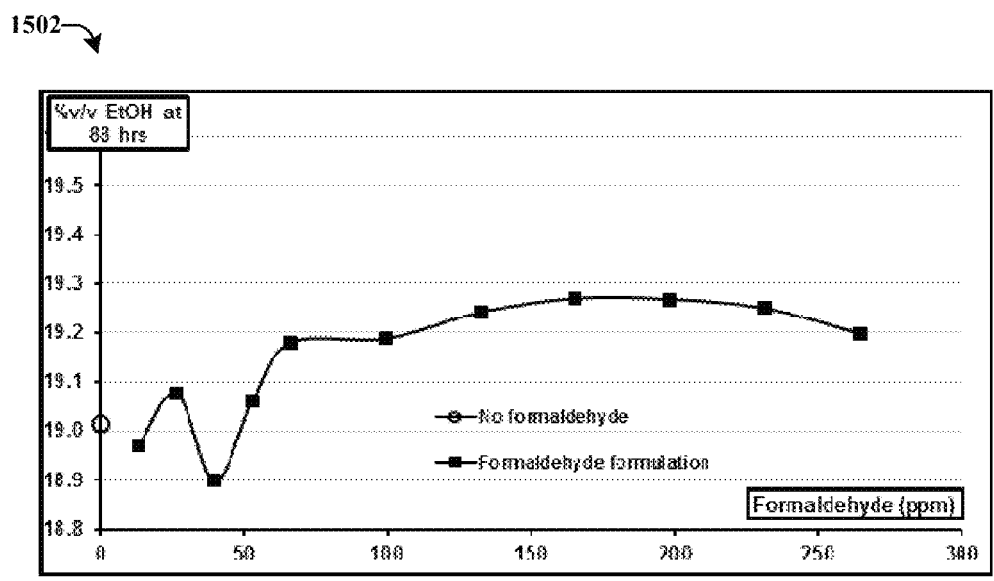
FIG. 15 is an example graph diagram illustrating ethanol production dependent upon formaldehyde priming dosage, in accordance with some embodiments.

FIG. 15 is an example graph diagram illustrating ethanol production dependent upon formaldehyde priming dosage. Percentage of ethanol generated is illustrated on the vertical axis 1502, while formaldehyde levels are illustrated along the horizontal axis 1504. The results showed that the levels of formaldehyde tested were slightly beneficial for yeast fermentation and ethanol production. The presence of formaldehyde affected the initial rate of ethanol production but did not adversely affect the final ethanol concentration. Note that at the levels used, there was no formaldehyde detected in the dried distillers grains, a co-product obtained from commercial corn-based ethanol production.

Example 4

In this fourth example, the impact of priming timing was further investigated. Once low levels of initial acetic acid proved beneficial for ethanol production, additional experiments were conducted to determine the best time for adding acetic acid to the fermenters. Knowledge of the best time for addition of acetic acid may be utilized to maximize ethanol production.

Standard laboratory cold cook fermentations at 36% dry solids were set up, as performed in examples 1 and 3. Different levels of acetic acid were added to the fermenters at different times after yeast inoculation.

Figure 16:
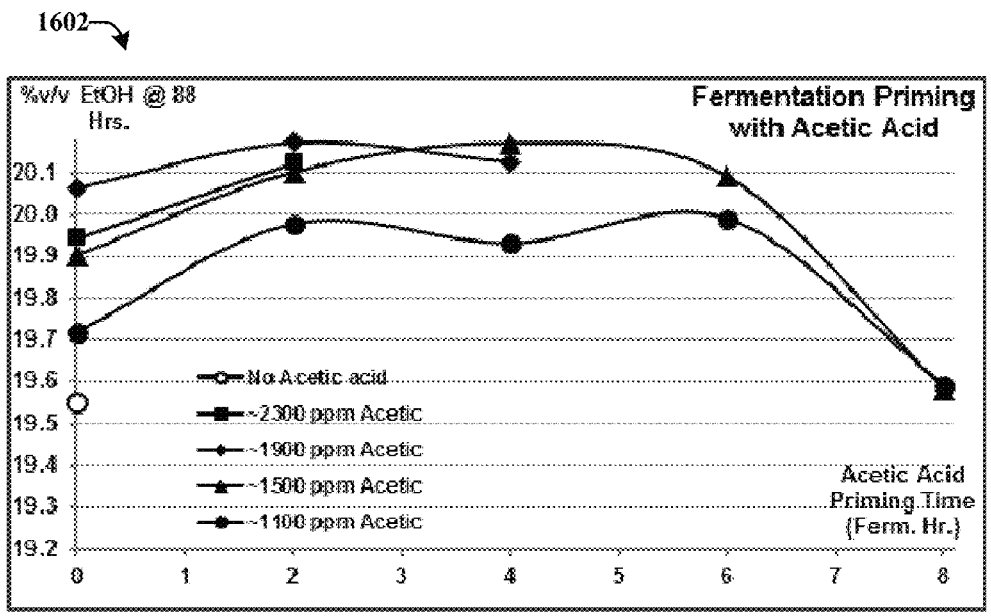
FIG. 16 is an example graph diagram illustrating ethanol yield dependent upon acid priming timing after yeast inoculation, in accordance with some embodiments.

FIG. 16 is an example graph diagram illustrating ethanol yield dependent upon acid priming timing after yeast inoculation. Ethanol yield is illustrated in reference to the vertical axis 1602. Timing of acetic acid addition after yeast inoculation is illustrated on the horizontal axis 1604. Examples for different acid concentrations are illustrated.

Based on the results obtained, when acetic acid is added to obtain an initial concentration of ≤1500 ppm the addition can be performed anytime between 1 and 6 hours after yeast inoculation to maximize ethanol production. When the acetic acid is added to obtain an initial concentration between 1900 and 2300 ppm, the addition can be performed anytime between 1 and 4 hours post yeast inoculation.

Example 5

In this final example, the impact of priming was explored in a commercial facility to gauge the scalability of priming results. In commercial ethanol production facilities, acetic acid is thought to be inhibitory to yeast growth and fermentation. Since the mechanism of action of acetic acid on yeast helps the acid to be stimulatory at low addition levels, a trial was conducted at a commercial ethanol producing biorefinery that practices a cold cook process. The dosage of acetic acid used is 320 gal per 720,000 gal fermentor or 250 gal per 550,000 gal fermentor and the acetic acid is added at 1.5 hours into fill of the fermentor (which would be about 1 hour after yeast inoculation from the yeast conditioning tank). The dosage of acetic acid for the industrial scale fermentors is calculated based off of the results obtained from lab scale testing, the fermentor fill time, and the uptake of acetic acid by the yeast during fermentor fill, as well as the dilution caused for the acetic acid concentration during fermentor fill. A few batches were conducted with added acetic acid (primed) and a few batches were operated normally without additional acetic acid. The corn mash in all the fermentors averaged 36% dry solids and the average fermentation time was 79±4 hours for all the test batches.

Figure 17:
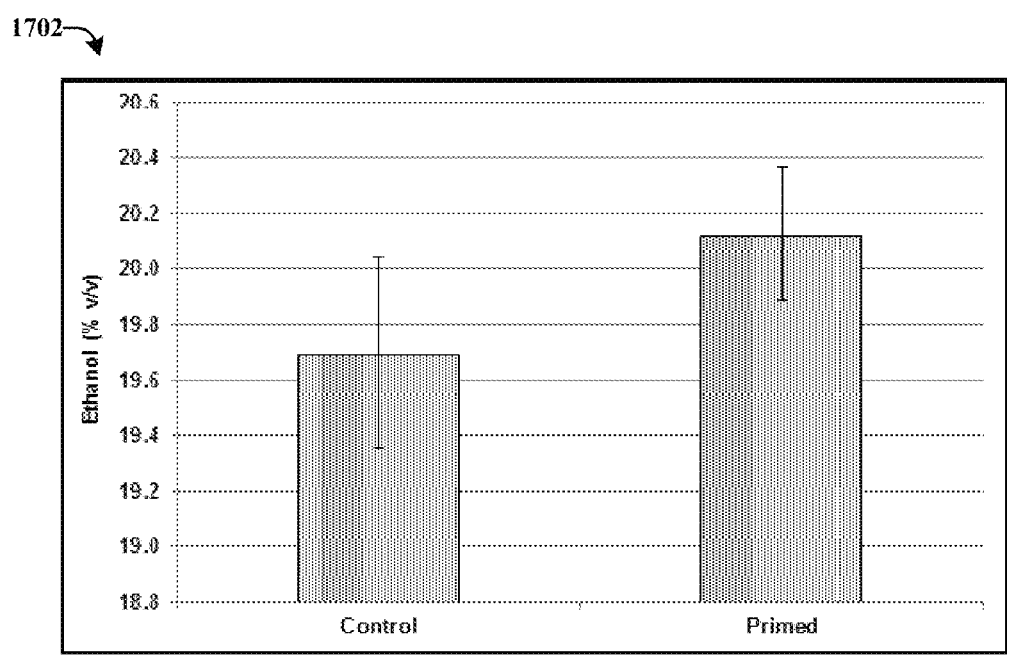
FIG. 17 is an example graph diagram illustrating ethanol production in a commercial ethanol production facility with and without acid priming, in accordance with some embodiments.

FIG. 17 is an example graph diagram illustrating ethanol production in a commercial ethanol production facility with and without acid priming. Percentage of ethanol for these commercial fermentations is illustrated in reference to the vertical axis 1702. Histogram bars are provided for no priming and primed samples, respectively, on the horizontal axis 1704. The results indicated increased ethanol production in the batches with acetic acid.

Figure 18:
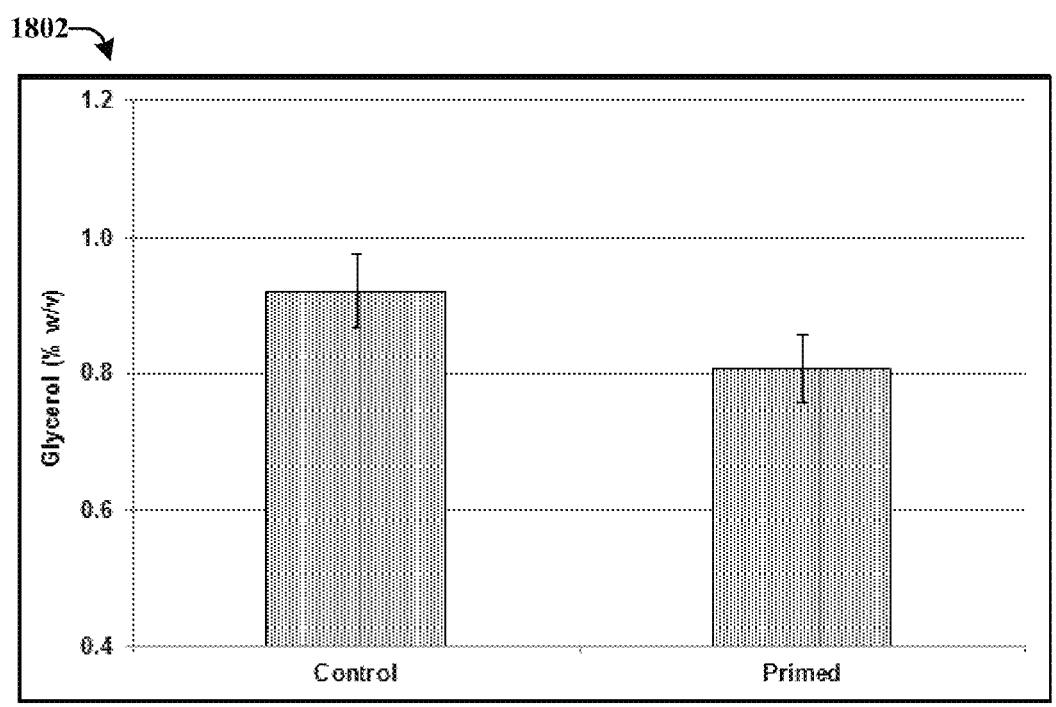
FIG. 18 is an example graph diagram illustrating glycerol production in a commercial ethanol production facility with and without acid priming, in accordance with some embodiments.

FIG. 18 is an example graph diagram illustrating glycerol production for these same batches. Percentage of glycerol produced for these commercial fermentations is illustrated in reference to the vertical axis 1802. Histogram bars are provided for no priming and primed samples, respectively, on the horizontal axis 1804. Clearly priming in this manner decreases glycerol production significantly.

The embodiments as disclosed and described in the application (including the FIGURES and Examples) are intended to be illustrative and explanatory of the disclosed aspects. Modifications and variations of the disclosed embodiments, for example, of the apparatus and processes employed (or to be employed) as well as of the compositions and treatments used (or to be used), are possible; all such modifications and variations are intended to be within the scope of the various aspects.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. A method for improving ethanol yield comprising:
   grinding a feedstock to generate a grind;
   combining the grind with water and enzymes to produce a slurry, wherein starch in the grind is converted to sugars in the slurry;
   adjusting the pH of the slurry to facilitate priming;
   adding an ethanologen to the slurry;
   priming the slurry by adding a priming agent 30 minutes to 120 minutes after adding the ethanologen to the slurry, wherein in the priming agent is added in addition to any supplemental priming agent produced by the ethanologen; and
   fermenting the slurry to produce ethanol.

2. The method as recited in claim 1, wherein the priming agent is an aldehyde.

3. The method as recited in claim 1, wherein the feedstock is corn.

4. The method as recited in claim 3, further comprising fractionating the corn into germ, endosperm, and bran.

5. The method as recited in claim 1, wherein the feedstock is ground to greater than 90% fines.

6. The method as recited in claim 1, wherein the slurry comprises about 35% solids.

7. The method as recited in claim 1, wherein the adjusting comprises adjusting the pH to between 4.2 and 52.

8. The method as recited in claim 1, wherein the slurry includes a backset, and at least some portion of the backset is thin stillage.

9. The method as recited in claim 1, wherein the ethanologen is *Saccharomyces cerevisiae*.

10. The method as recited in claim 1, wherein the priming agent is acetic acid.

11. The method as recited in claim 10, further comprising adding the acetic acid at a concentration of between 1200 and 3600 parts per million.

12. The method as recited in claim 10, further comprising adding the acetic acid at a concentration of between 1800 and 2400 parts per million.

13. A method for improving ethanol yield comprising:
    grinding a feedstock to generate a grind;
    combining the grind with water and enzymes to produce a slurry, wherein starch in the grind is converted to sugars in the slurry;
    removing a portion of the slurry, thereby leaving behind a remainder of the slurry;
    adjusting the pH of the portion of the slurry to facilitate priming;
    adding an ethanologen to the portion of the slurry;
    priming the portion of the slurry by adding a priming agent 30 minutes to 120 minutes after adding the ethanologen to the slurry, wherein in the priming agent is added in addition to any supplemental priming agent produced by the ethanologen;
    combining the portion of the slurry with the remainder of the slurry; and
    fermenting the slurry to produce ethanol.

14. The method as recited in claim 13, wherein the priming agent is one of a weak acid and formaldehyde.

15. The method as recited in claim 13, wherein the feedstock is ground to greater than 90% fines.

16. The method as recited in claim 14, wherein the feedstock is corn.

17. The method as recited in claim 16, further comprising fractionating the corn into germ, endosperm, and bran.

18. The method as recited in claim 13, wherein the slurry comprises about 35% solids.

19. The method as recited in claim 13, wherein the adjusting comprises adjusting the pH to between 4.2 and 5.2.

20. The method as recited in claim 13, wherein the slurry includes a backset, and at least some portion of the backset is thin stillage.

21. The method as recited in claim 13, wherein the ethanologen is *Saccharomyces cerevisiae*.

22. The method as recited in claim 13, wherein the priming agent is acetic acid.

23. The method as recited in claim 22, wherein the acetic acid is added at a concentration of between 1200 and 2400 parts per million of the portion of the slurry.

24. The method as recited in claim 23, further comprising holding the portion of the slurry between 1200 and 2400 parts per million of acetic acid for at least 10 minutes prior to combining the portion of the slurry with the remainder of the slurry.

* * * * *